(12) United States Patent
Fischer et al.

(10) Patent No.: US 9,718,752 B2
(45) Date of Patent: *Aug. 1, 2017

(54) PROCESS FOR THE SEPARATION OF AN ALKYLENE GLYCOL

(71) Applicant: SHELL OIL COMPANY, Houston, TX (US)

(72) Inventors: Kai Jürgen Fischer, Amsterdam (NL); Wouter Koot, Amsterdam (NL); Arlette Wesenhagen, Amsterdam (NL); Roel Guillaume Hubertus Leonardus Bastings, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/893,273

(22) PCT Filed: May 28, 2014

(86) PCT No.: PCT/EP2014/061158
§ 371 (c)(1),
(2) Date: Nov. 23, 2015

(87) PCT Pub. No.: WO2014/191509
PCT Pub. Date: Dec. 4, 2014

(65) Prior Publication Data
US 2016/0102035 A1    Apr. 14, 2016

(30) Foreign Application Priority Data

May 31, 2013    (EP) ..................................... 13169982

(51) Int. Cl.
| C07C 41/38 | (2006.01) |
| C07C 29/80 | (2006.01) |
| C07C 41/42 | (2006.01) |
| C07C 29/86 | (2006.01) |

(52) U.S. Cl.
CPC .............. *C07C 41/38* (2013.01); *C07C 29/80* (2013.01); *C07C 29/86* (2013.01); *C07C 41/42* (2013.01)

(58) Field of Classification Search
None
See application file for complete search history.

(56) References Cited

U.S. PATENT DOCUMENTS

| 2,831,801 | A | 4/1958 | Beckham et al. |
| 4,032,583 | A | 6/1977 | Arganbright et al. |
| 4,081,354 | A | 3/1978 | Christman |
| 4,447,643 | A | 5/1984 | Feldman |
| 4,966,658 | A | 10/1990 | Berg |
| 5,387,731 | A | 2/1995 | Jenkins et al. |
| 5,423,955 | A | 6/1995 | Berg |
| 6,023,003 | A | 2/2000 | Dunning et al. |
| 8,067,214 | B2 | 11/2011 | Burk et al. |
| 2005/0072663 | A1 | 4/2005 | Laborie et al. |
| 2009/0171129 | A1 | 7/2009 | Evanko et al. |
| 2011/0312050 | A1 | 12/2011 | Zhang et al. |
| 2012/0018293 | A1 | 1/2012 | Kaasa et al. |
| 2012/0184783 | A1 | 7/2012 | Barnicki |
| 2013/0284584 | A1 | 10/2013 | Xiao et al. |

FOREIGN PATENT DOCUMENTS

| CN | 1216973 | 5/1999 |
| CN | 01959568 | 1/2011 |
| CN | 102295384 | 12/2011 |
| CN | 102643165 | 8/2012 |
| CN | 103396290 | 11/2013 |
| CN | 103664522 | 3/2014 |
| CN | 103772147 | 5/2014 |
| CN | 103772148 | 5/2014 |
| EP | 0844228 | 5/1998 |
| JP | 5640625 | 12/2014 |
| WO | 9519946 | 7/1995 |
| WO | 2002022593 | 3/2002 |
| WO | 2010080038 | 7/2010 |
| WO | 2011028131 | 3/2011 |
| WO | 2012041990 | 4/2012 |
| WO | 2012130316 | 10/2012 |
| WO | 2013011462 | 1/2013 |

OTHER PUBLICATIONS

Garcia-Chavez, et al.; "COSMO-RS assisted solvent screening for loiquid-liquid extraction of mono ethylene glycol from aqueous streams", Separation and Purification Technology, vol. 97, Sep. 3, 2012, pp. 2-10, XP002716373.
Hoydonckx, H.E, et al= Furfural and Derivatives, in Ulmann' s Encyclopedia or Industrial Chemistry, vol. 16, pp. 285-313, 2012.
Lange, Jean-Paul, et al.; Furfural—A Promisign Platform for Lignocellulosic Biofuels, ChemSusChem 2012, pp. 150-166.
Watson J M et al.:Butane=1,4=diol from Hydrolytic Reduction of Furan.
Zeitsch, Karl, J: The chemistry and technology of furfural and its many by-products. Elsevier, 2000.
Ghanadzadeh, et al.: Experimental and Theoretical Study of the Phase Equilibria in Ternary Aqueous Mixtures of 1,4-Butanediol with Alcohols at 298.2 K j CHEM ENG., 2009, 54, pp. 1009-1014.
Guan, Weihong: Heilongjiang Petrochemical Technology, vol. 11, No. 4, Dec. 31, 2000 The preparation and application of 1,4-butanediol, pp. 9-11, 1-16,18-19, English translation of abstract.

*Primary Examiner* — Rosalynd Keys (57) ABSTRACT

The invention provides a process for the recovery of an alkylene glycol from an aqueous stream comprising the alkylene glycol and the corresponding dialkylene glycol, said process comprising the steps of providing the aqueous stream comprising the alkylene glycol and the corresponding dialkylene glycol, providing a first solvent stream, combining said aqueous stream comprising the alkylene glycol and the corresponding dialkylene glycol with said first solvent stream and recovering at least a portion of the alkylene glycol by liquid-liquid extraction, wherein said solvent comprises an amine.

19 Claims, 4 Drawing Sheets

PROCESS FOR THE SEPARATION OF AN ALKYLENE GLYCOL

PRIORITY CLAIM

The present application is the National Stage (§371) of International Application No. PCT/EP2014/061158, filed May 28, 2014, which claims benefit from European Application No. 13169982.9, filed May 31, 2013, both of which are incorporated herein by reference.

FIELD OF THE INVENTION

The present invention relates to a process for the separation of an alkylene glycol.

BACKGROUND OF THE INVENTION

Ethylene glycol and propylene glycol are valuable materials with a multitude of commercial applications. Ethylene glycol, commonly known as monoethylene glycol (MEG), is used as a raw material in the manufacture of polyester fibres, polyethylene terephthalate (PET) plastics and resins. It is also incorporated into automobile antifreeze liquids.

MEG is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide can then be converted into MEG. In one well-known process, the ethylene oxide is reacted with a large excess of water in a non-catalytic process. This reaction typically produces a glycol product stream, after removal of water, consisting of almost 90 weight percent MEG, the remainder being predominantly diethylene glycol (DEG), some triethylene glycol (TEG) and a small amount of higher homologues. In another well-known process, ethylene oxide is reacted with a smaller excess of water in the presence of a hydrolysis catalyst. In a further well-known process, ethylene oxide is catalytically reacted with carbon dioxide to produce ethylene carbonate. The ethylene carbonate is subsequently hydrolysed to provide ethylene glycol. Reaction via ethylene carbonate can improve the selectivity to monoethylene glycol, although diethylene glycols and higher ethylene glycols, such as triethylene glycol and tetraethylene glycol (TTEG) will still be present in the produced glycol product stream.

The ethylene glycol-containing aqueous streams that result from the known processes are subjected to water removal, typically in a series of flashing and/or distillation steps. The water removal is an energy intensive process, particularly if a large excess of water is present in the ethylene glycol-containing streams. After water removal, further distillation steps are then required in order to purify the MEG and separate the DEG, TEG and higher homologues. Distillation of glycols at high temperature can lead to decomposition and the production of quantities of by-products. Therefore, the distillation of glycols is generally carried out under reduced pressure, further increasing the energy requirement for purification.

A process for the extraction of MEG and propylene glycol from aqueous streams using ionic liquids, particularly tetraethyl ammonium-2-methyl-1-naphthoate is described in both Ind. Eng. Chem. Res. 2013, 52, 4902 and Separation and Purification Technology, 2012, 97, 2. However, the use of such high-boiling ionic liquids will provide further issues relating to the purification of materials after liquid-liquid extraction. High-boiling impurities will accumulate in the ionic liquids on repeated use, reducing their potential recyclability. Further, ionic liquids tend to have high viscosities leading to handling and mixing problems.

The present inventors have sought to provide a process for the facile separation of alkylene glycols, particularly ethylene glycol in which the large distillation duty required in the water removal and subsequent purification of the remaining glycols is significantly reduced and in which materials are easily re-used in an industrial process.

SUMMARY OF THE INVENTION

Accordingly, the present invention provides a process for the recovery of an alkylene glycol from an aqueous stream comprising the alkylene glycol and the corresponding dialkylene glycol, said process comprising the steps of providing the aqueous stream comprising the alkylene glycol and the corresponding dialkylene glycol, providing a first solvent stream, combining said aqueous stream comprising the alkylene glycol and the corresponding dialkylene glycol with said first solvent stream and recovering at least a portion of the alkylene glycol by liquid-liquid extraction, wherein said solvent stream comprises an amine.

DETAILED DESCRIPTION OF THE INVENTION

The present inventors have surprisingly found that alkylene glycols may be recovered from an aqueous stream comprising a mixture of the alkylene glycol with the corresponding dialkylene glycols, optionally higher alkylene glycols and also optionally salts, by the use of a solvent and liquid-liquid extraction. This process avoids the large distillation duty required in standard glycol recovery processes known in the art. The process of the invention also allows for the facile separation of dialkylene glycols and higher alkylene glycols either together with the alkylene glycol or individually, depending on the requirements of the system.

The term alkylene glycol, as used herein, refers to monoalkylene glycols. The alkylene glycol in the process of the invention is suitably of the formula:

wherein $R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkylene glycols therefore include ethylene glycol and propylene glycol. In the present invention the most preferred alkylene glycol is ethylene glycol.

Dialkylene glycols are dimers of the corresponding alkylene glycols. Diethylene glycol, for example, is a dimer of ethylene glycol and has the formula HO—$CH_2$—$CH_2$—O—$CH_2$—$CH_2$—OH. Higher alkylene glycols comprise trimers, tetramers, etc of the corresponding alkylene glycols. Triethylene glycol, for example, is a trimer of ethylene glycol and has the formula HO—$CH_2$—$CH_2$—O—$CH_2$—$CH_2$—O—$CH_2$—$CH_2$—OH. These dimers, trimers, and higher oligomers are often formed during the hydrolysis reaction of alkylene oxides and are produced when an alkylene oxide reacts with a glycol present in the reaction mixture rather than water.

The aqueous stream comprising the alkylene glycol and the corresponding dialkylene glycol will preferably also comprise corresponding higher alkylene glycols.

Preferably, the stream comprising the alkylene glycol and the corresponding dialkylene glycol is the reaction product stream from a process for the conversion of an alkylene oxide to the corresponding alkylene glycol. The process for the conversion of an alkylene oxide to the corresponding alkylene glycol may be any suitable process including, but not limited to, the direct, catalytic or non-catalytic, hydrolysis of the alkylene oxide, or the conversion of an alkylene oxide to the corresponding alkylene glycol via the corresponding alkylene carbonate. In one embodiment of the invention, the aqueous stream will also contain salts, preferably comprising catalyst material from a process to produce alkylene glycols from the corresponding alkylene oxides.

The alkylene glycol is typically present in the aqueous stream in the range of from 5 to 99.9 wt % based on the overall weight of the stream, depending on the process used to produce the alkylene glycol. In one embodiment of the invention, the alkylene glycol is ethylene glycol produced by non-catalytic direct hydrolysis of ethylene oxide. In this embodiment, the aqueous stream will preferably contain at least 5, more preferably at least 7 wt % of ethylene glycol and at most 20, more preferably at most 15 wt % of ethylene glycol based on the overall weight of the stream.

In a further embodiment of the invention, the alkylene glycol is ethylene glycol produced by a catalytic direct hydrolysis process from ethylene oxide. In this embodiment, the aqueous stream will preferably contain at least 5, more preferably at least 10 wt % of ethylene glycol and at most 50, more preferably at most 30 wt % of ethylene glycol based on the overall weight of the stream.

In another embodiment of the invention, the alkylene glycol is ethylene glycol produced by a catalytic process in which ethylene oxide is first converted to the carbonate, which is then hydrolysed to the glycol. In this embodiment, the aqueous stream will preferably contain at least 60 wt %, more preferably at least 70 wt % of ethylene glycol, based on the overall weight of the stream. Also in this embodiment, the aqueous stream will preferably contain at most 99.9 wt %, more preferably at most 99 wt %, even more preferably at most 90 wt %, most preferably at most 85 wt % of ethylene glycol, based on the overall weight of the stream.

The dialkylene glycol is preferably present in the aqueous stream in an amount of at least 0.1 wt %, preferably at least 0.5 wt %, based on the overall weight of the stream. The dialkylene glycol is preferably present in the aqueous stream in an amount of at most 3 wt %, more preferably at most 2 wt %, even more preferably at most 1.5 wt % based on the overall weight of the stream. Again, the amounts will vary depending on the process used for the production of the alkylene glycol.

Higher alkylene glycols, if present, are typically present in the aqueous stream in the range of from 0.01 to 1 wt % based on the overall weight of the stream. Again, the amounts will vary depending on the process used for the production of the alkylene glycol.

As well as the alkylene glycol, the corresponding dialkylene glycol and, if present, the higher alkylene glycols, the reaction product streams from a process for the conversion of an alkylene oxide to the corresponding alkylene glycol may comprise water, oxygenates, hydrocarbons, catalyst, degradation products, and gases in any composition. When the alkylene glycol is monoethylene glycol, materials present may typically include ethylene oxide, water, traces of oxygenates (for example acetaldehyde, formaldehyde and glycolaldehydes), carbon dioxide, catalysts (iodides, carbonates) and chlorides.

The process of the invention is preferably carried out at a temperature of at least 5° C., more preferably at least 10° C., even more preferably at least 20° C., even more preferably at least 25° C., most preferably at least 50° C. The temperature is preferably at most 250° C., more preferably at most 200° C., even more preferably at most 150° C. The pressure is preferably in the range of from 0.1 to 10 MPa, more preferably in the range of from 0.1 to 2.5 MPa, even more preferably in the range of from 0.1 to 1 MPa and must suitably be high enough to avoid vaporisation of the materials.

The first solvent stream comprises an amine as a solvent. 'Amine' as used herein refers to one or more amine used as the solvent in the solvent stream. The term 'solvent' as used herein refers to this amine or mixture of amines. Suitably, the amine has a higher affinity for the alkylene glycol than water. Also suitably, the amine shows a liquid-liquid phase split when mixed with water or saline water at appropriate process temperatures, preferably in the range of from 0 to 250° C. Preferably, the amine comprises one or more alkyl amines. More preferably, the amine comprises a primary, a secondary, a tertiary alkyl amine, or a combination thereof. Preferably, the amine is a tertiary alkyl amine. Examples of suitable alkyl amines include paraffinic amines, naphthenic amines, aromatic amines, and mixtures thereof.

Preferably, the amine contains carbon and nitrogen atoms in a ratio of at most 8:1 (carbon:nitrogen atoms).

Preferably, the amine contains an aliphatic cyclic group either containing the amine nitrogen or attached to the amine nitrogen.

More preferably, the amine is selected from the group consisting of N,N-dimethylcyclohexylamine (DMCA), methyl cyclohexyl amine, N-methyl piperidine, triethylamine, tripropylamine, or a combination thereof.

The first solvent stream may be added to or combined with the aqueous stream comprising the alkylene glycol and the corresponding dialkylene glycol in any amount sufficient to allow a portion of the alkylene glycol to dissolve in the solvent. Water may also dissolve in the solvent stream to the extent that the glycol to water ratio in the extract stream is larger than in the aqueous stream comprising the alkylene glycol and the corresponding dialkylene glycol. In certain embodiments, the amount of solvent added to or combined with the aqueous stream comprising the alkylene glycol and the corresponding dialkylene glycol may be from 10 to 500 wt % of the total content of that stream.

Preferably, the ratio of solvent to alkylene glycol may be in the range of from the minimum amount for exceeding the solubility limit of the solvent in the aqueous stream comprising the alkylene glycol and the corresponding dialkylene glycol to less than the amount needed to dissolve the entire aqueous stream comprising the alkylene glycol and the corresponding dialkylene glycol.

The amount of solvent added to or combined with the aqueous stream comprising the alkylene glycol and the corresponding dialkylene glycol may suitably be at least 10 wt %, preferably at least 20 wt %, more preferably at least 25 wt % of the amount of alkylene glycol in the aqueous stream comprising the alkylene glycol and the corresponding dialkylene glycol. The amount of solvent added to or combined with the aqueous stream comprising the alkylene glycol and the corresponding dialkylene glycol may suitably be at most 2000 wt %, preferably at most 500 wt %, more preferably at most 100 wt % of the amount of alkylene glycol in the aqueous stream comprising the alkylene glycol and the corresponding dialkylene glycol.

The aqueous stream comprising the alkylene glycol and the corresponding dialkylene glycol is combined with the first solvent stream by any method suitable for the combination of two liquid streams, including but not limited to using a stirred mixer, passing the streams through a static mixer or by agitation. State of the art liquid-liquid contactors (extraction units) are, for example, a series of mixers and settlers, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the two streams are combined in a counter-current extraction unit. In such a unit, the two streams are fed to the unit at separate points and are brought into contact with each other while passing through the unit in a counter-current fashion.

The alkylene glycol is recovered from the aqueous stream comprising the alkylene glycol and the corresponding dialkylene glycol by liquid-liquid extraction after the first solvent stream has been added to or combined with the aqueous stream comprising the alkylene glycol and the corresponding dialkylene glycol. For example, after the first solvent stream has been added to or combined with the aqueous stream comprising the alkylene glycol and the corresponding dialkylene glycol, a portion of the alkylene glycol may be extracted into the solvent. The solvent, along with the alkylene glycol, may then be separated from the rest of the aqueous stream comprising the alkylene glycol and the corresponding dialkylene glycol, forming an alkylene glycol and solvent rich stream and a first residual stream.

Preferably, any salt remains dissolved in the aqueous stream comprising the alkylene glycol and the corresponding dialkylene glycol and the first residual stream so that the separation process happens without precipitation of salts. This is particularly preferred wherein the salts are catalytic materials that may be recycled with at least part of the aqueous first residual stream to the process for the production of the alkylene glycol.

In certain embodiments, the liquid-liquid extraction may be enhanced by the inclusion of a synergist. Examples of suitable synergist include demulsifiers. Typical demulsifiers may include phenol-formaldehyde resins, epoxy resins, polyamines, di-epoxides or polyols.

Preferably, the method further comprises recovering the alkylene glycol and/or solvent from the alkylene glycol and solvent rich stream. The alkylene glycol and/or solvent may be recovered from the alkylene glycol and solvent rich stream through a distillation process. In certain embodiments, the solvent or the alkylene glycol may be recovered as the distillate or bottom product. In certain embodiments, the alkylene glycol and solvent rich stream may be distilled to form an alkylene glycol rich stream and a first solvent rich stream. Preferably, the solvent in the first solvent rich stream is separated from any water present therein by a process comprising phase separation, more preferably after condensing said stream and/or cooling said stream to below the process temperature. Optionally, the solvent may then be recycled.

Preferably, the alkylene glycol rich stream is recovered as a stream that contains essentially no amine, either after the distillation step or after a subsequent purification step.

In one embodiment of the invention, dialkylene glycol and, optionally, higher alkylene glycols are also separated from the aqueous stream comprising the alkylene glycol and the corresponding dialkylene glycol and are present in the alkylene glycol and solvent rich stream. This results in facile separation of all of the glycols from the water and they can then be separated, suitably by distillation, after removal of the amine solvent. It is preferred, however, that the alkylene glycol is selectively removed from the aqueous stream comprising the alkylene glycol and the corresponding dialkylene glycol and that the dialkylene glycol and, if present, the higher alkylene glycols remain in the first residual stream.

In a preferred embodiment of the invention, after recovering the alkylene glycol according to the process of the invention, the dialkylene glycol is subsequently recovered from the first residual stream by a process comprising the steps of providing the first residual stream, providing a second solvent stream, combining said first residual stream with said second solvent stream and recovering at least a portion of the dialkylene glycol by liquid-liquid extraction, wherein the solvent stream comprises an amine.

The solvent in the second solvent stream may be added to or combined with the first residual stream in any amount sufficient to allow a portion of the dialkylene glycol to dissolve in the solvent. Water may also dissolve in the solvent stream to the extent that the glycol to water ratio in the extract stream is larger than in the first residual stream. In certain embodiments, the amount of solvent added to or combined with the first residual stream may be from 10 to 500 wt % of the total content of that stream.

Preferably, the ratio of solvent to dialkylene glycol may be in the range of from the minimum amount for exceeding the solubility limit of the solvent in the first residual stream to less than the amount needed to dissolve the entire first residual stream.

The amount of solvent added to or combined with the first residual stream may suitably be at least 10 wt %, preferably at least 20 wt %, more preferably at least 25 wt % of the amount of dialkylene glycol in the first residual stream. The amount of solvent added to or combined with the first residual stream may suitably be at most 2000 wt %, preferably at most 500 wt %, more preferably at most 100 wt % of the amount of dialkylene glycol in the first residual stream.

The second solvent stream may comprise any of the same solvents as indicated as suitable for the first solvent stream. Preferably the second solvent stream comprises the same solvent as used in the first solvent stream. The second solvent stream may be introduced as a separate stream, or it may be formed from at least a portion of the solvent remaining after the alkylene glycol and solvent rich stream has been removed.

The first residual stream is combined with the second solvent stream by any method suitable for the combination of two liquid streams, including but not limited to using a stirred mixer, passing the streams through a static mixer or by agitation. State of the art liquid-liquid contactors (extraction units) are, for example, a series of mixers and settlers, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the two streams are combined in a counter-current extraction unit. In such a unit, the two streams are fed to the unit at separate points and are brought into contact with each other while passing through the unit in a counter-current fashion.

The dialkylene glycol is recovered from the first residual stream by liquid-liquid extraction after the second solvent stream has been added to or combined with the first residual stream. For example, after the second solvent stream has been added to or combined with the first residual stream, a portion of the dialkylene glycol may be extracted into the solvent therein. This solvent, along with the dialkylene glycol, may then be separated from the rest of the first residual stream forming a dialkylene glycol and solvent rich stream and a second residual stream.

Preferably, any salt remains dissolved in the first and second residual streams so that the separation process happens without precipitation of salts. This is particularly preferred wherein the salts are catalytic materials that may be recycled with at least part of the aqueous second residual stream to the process for the production of the alkylene glycol.

In certain embodiments, the liquid-liquid extraction may be enhanced by the inclusion of a synergist. Examples of suitable synergist include demulsifiers. Typical demulsifiers may include phenol-formaldehyde resins, epoxy resins, polyamines, di-epoxides or polyols.

Preferably, the method further comprises recovering the dialkylene glycol and/or solvent from the dialkylene glycol and solvent rich stream. The dialkylene glycol and/or solvent may be recovered from the dialkylene glycol and solvent rich stream through a distillation process. In certain embodiments, the solvent or the dialkylene glycol may be recovered as the distillate or bottom product. In certain embodiments, the dialkylene glycol and solvent rich stream may be distilled to form a dialkylene glycol rich stream and a second solvent rich stream. Preferably, the solvent in the second solvent rich stream is separated from any water present therein by a process comprising phase separation, more preferably after condensing said stream and/or cooling said stream to below the process temperature. Optionally, the solvent from the second solvent rich stream may then be recycled.

Preferably, the dialkylene glycol rich stream is recovered as a stream that contains substantially no amine, either after the distillation step or after a subsequent purification step.

In one embodiment of the invention, higher alkylene glycols are also separated from the first residual stream and are present in the dialkylene glycol and solvent rich stream. As dialkylene glycol and higher alkylene glycols are considered by-products and are present in relatively low amounts, it may be advantageous to separate the desirable alkylene glycol using the process of the invention in a first step and then separate the small amount of di- and higher alkylene glycols together in a second step before separating the dialkylene glycols and higher alkylene glycols from each other by conventional means. It is preferred, however, that the dialkylene glycol is selectively removed from the first residual stream and that the higher alkylene glycols remain in the second residual stream.

In a preferred embodiment of the invention, after recovering the dialkylene glycol according to the process of the invention, at least one higher alkylene glycol is subsequently recovered from the second residual stream by a process comprising the steps of providing the second residual stream, providing a third solvent stream, combining said second residual stream with said third solvent stream and recovering at least a portion of the higher alkylene glycol or glycols by liquid-liquid extraction, wherein the third solvent stream comprises an amine.

The solvent in the third solvent stream may be added to or combined with the second residual stream in any amount sufficient to allow a portion of the higher alkylene glycol or glycols to dissolve in the solvent. Water may also dissolve in the solvent to the extent that the glycol to water ratio in the extract stream is larger than in the second residual stream. In certain embodiments, the amount of solvent added to or combined with the second residual stream may be from 10 to 500 wt % of the total content of that stream.

Preferably, the ratio of solvent to higher alkylene glycol or glycols may be in the range of from the minimum amount for exceeding the solubility limit of the solvent in the second residual stream to less than the amount needed to dissolve the entire second residual stream.

The amount of solvent added to or combined with the second residual stream may suitably be at least 10 wt %, preferably at least 20 wt %, more preferably at least 25 wt % of the amount of higher alkylene glycol or glycols in the second residual stream. The amount of solvent added to or combined with the second residual stream may suitably be at most 2000 wt %, preferably at most 500 wt %, more preferably at most 100 wt % of the amount of higher alkylene glycol or glycols in the second residual stream.

The third solvent stream may comprise any of the same solvents as indicated as suitable for the first and second solvent streams. Preferably the third solvent stream comprises the same solvent as used in the first and second solvent streams. The third solvent stream may be introduced as a separate stream, or it may be formed from at least a portion of the solvent remaining after the dialkylene glycol and solvent rich stream has been removed.

The second residual stream is combined with the third solvent stream by any method suitable for the combination of two liquid streams, including but not limited to using a stirred mixer, passing the streams through a static mixer or by agitation. State of the art liquid-liquid contactors (extraction units) are, for example, a series of mixers and settlers, agitated extraction columns, packed extraction columns, SCHEIBEL® Columns, KARR® Columns, rotating disc contactor (RDC) columns, pulsed, packed (SMVP) and sieve tray columns. In a preferred embodiment of the invention, the two streams are combined in a counter-current extraction unit. In such a unit, the two streams are fed to the unit at separate points and are brought into contact with each other while passing through the unit in a counter-current fashion.

The higher alkylene glycol or glycols are recovered from the second residual stream by liquid-liquid extraction after the third solvent stream has been added to or combined with the second residual stream. For example, after the third solvent stream has been added to or combined with the second residual stream, a portion of the higher alkylene glycol or glycols may be extracted into the solvent therein. This solvent, along with the higher alkylene glycol or glycols, may then be separated from the rest of the second residual stream forming a higher alkylene glycol or glycols and solvent rich stream and a third residual stream.

Preferably, any salt remains dissolved in the first and second residual streams so that the separation process happens without precipitation of salts. This is particularly preferred wherein the salts are catalytic materials that may be recycled with at least part of the aqueous third residual stream to the process for the production of the alkylene glycol.

In certain embodiments, the liquid-liquid extraction may be enhanced by the inclusion of a synergist. Examples of suitable synergist include demulsifiers. Typical demulsifiers may include phenol-formaldehyde resins, epoxy resins, polyamines, di-epoxides or polyols.

Preferably, the method further comprises recovering the higher alkylene glycol or glycols and/or solvent from the higher alkylene glycol or glycols and solvent rich stream. The higher alkylene glycol or glycols and/or solvent may be recovered from the higher alkylene glycol or glycols and solvent rich stream through a distillation process. In certain embodiments, the solvent or the higher alkylene glycol or glycols may be recovered as the distillate or bottom product. In certain embodiments, the higher alkylene glycol or glycols and solvent rich stream may be distilled to form a higher alkylene glycol or glycols rich stream and a third solvent rich stream. Preferably, the solvent in the third solvent rich stream is separated from any water present therein by a process comprising phase separation, more preferably after condensing said stream and/or cooling said stream to below the process temperature. Optionally, the solvent from the third solvent rich stream may then be recycled.

Preferably, the higher alkylene glycol or glycols rich stream is recovered as a stream that contains substantially no amine, either after the distillation step or after a subsequent purification step.

The amine used in each of the first, second and third solvent streams may be the same or different. In a particularly preferred embodiment of the invention, the amine used in the recovery of the dialkylene glycol is the same as the amine used in the recovery of the alkylene glycol. In this embodiment it is particularly advantageous to use an amine which is more selective to the alkylene glycol than to the dialkylene glycol. An example of an amine solvent that is more selective to an alkylene glycol than to the corresponding dialkylene glycol is dimethylcyclohexylamine, which has been shown to be more selective to ethylene glycol than to diethylene glycol.

It is even more preferred that the amine used in the recovery of the higher alkylene glycol or glycols is the same as used in the recovery of the dialkylene glycol. In this embodiment it is particularly advantageous to use an amine which is more selective to the dialkylene glycol than to the higher alkylene glycol or glycols.

It is preferred that the aqueous first, second and/or third residual streams are recycled back to the process for the production of the alkylene glycol, either separately or after combination of two or more of the streams. In this embodiment of the invention, it is preferable that the aqueous stream or streams to be recycled are essentially free of the amine. This may be achieved in the liquid-liquid separation or in a separate purification step before recycle. In a particularly preferred embodiment of the invention, wherein the first, second and/or third residual streams contain catalytic materials in the form of salts, the stream or streams may be recycled after concentration of the stream by removal of a portion of the water contained therein. This concentration step may be carried out by distillation or by filtration and/or membrane separation. Preferably, the concentration is carried out by filtration and/or membrane separation, avoiding the additional distillation duty.

It may be preferable to remove a bleed stream comprising a portion of the recycled aqueous stream or streams and/or the recycled amine solvent stream or streams in order to prevent the build up of any trace components present in these streams.

Figure 1:
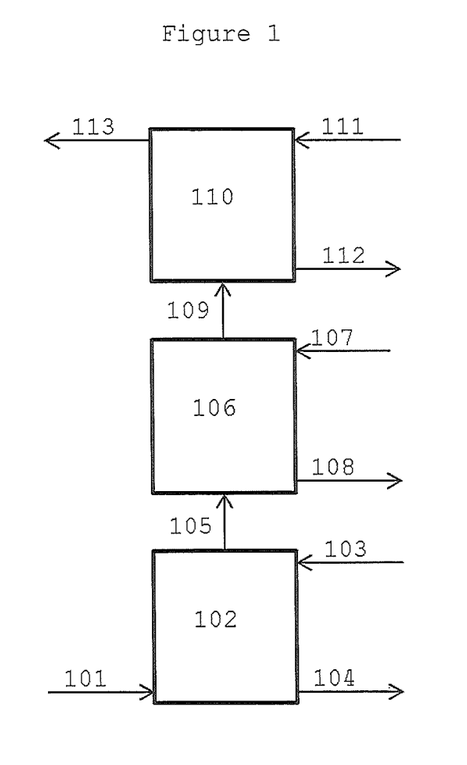
FIGS. 1, 2 and 3 are schematic diagrams showing non-limiting embodiments of the invention.

In a preferred, but non-limiting, embodiment of the invention illustrated in FIG. 1, the aqueous stream comprising the alkylene glycol and the corresponding dialkylene glycol comprises the reaction product stream from a process for the preparation of ethylene glycol from ethylene oxide. The stream contains at least MEG, DEG, TEG and higher ethylene glycols. This stream 101 is fed into a counter-current extraction unit comprising three extraction stages. The stream 101 is introduced to a first extraction stage 102, where it is contacted in a counter-current manner with a first solvent stream 103. An alkylene glycol and solvent rich stream 104 is removed and a first residual stream 105 is passed to a second extraction stage 106. In the second extraction stage 106, the first residual stream is contacted in a counter-current manner with a second solvent stream 107. A dialkylene glycol and solvent rich stream 108 is removed and a second residual stream 109 is passed to a third extraction stage 110. In the third extraction stage 110, the second residual stream is contacted in a counter-current manner with a third solvent stream 111. A higher alkylene glycol and solvent rich stream 112, comprising TEG and, optionally higher alkylene glycols, is removed and a third residual stream 113 is also removed for further purification, recycle or disposal.

It will be readily understood by the skilled person that FIG. 1 is merely a schematic representation of the process of the invention. The actual set-up and orientation, e.g. vertical, horizontal, upward flow, downward flow, of the materials and units involved will depend on the conditions and materials used, including the density difference between the materials used.

Each glycol and solvent rich stream can be separately treated to provide the glycol and the solvent, suitably by distillation. It will be readily understood by the skilled person that each extraction stage may incorporate multiple steps of adding a solvent stream, contacting it with the aqueous stream comprising the alkylene glycol and the corresponding dialkylene glycol or the residual stream and separating a glycol and solvent rich stream. Further, the individual extraction stages may be in separate vessels or may be contained within a single vessel.

Figure 2:
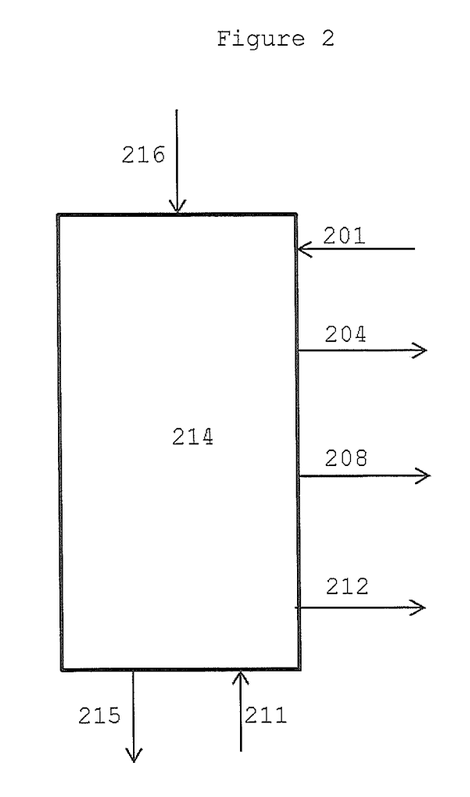

In a further preferred, but non-limiting, embodiment illustrated in FIG. 2, the aqueous stream comprising the alkylene glycol and the corresponding dialkylene glycol comprises the reaction product stream from a process for the preparation of ethylene glycol from ethylene oxide. The stream contains at least MEG, DEG, TEG and higher ethylene glycols. This stream 201 is fed into a counter-current extraction unit 214. Said extraction unit is also fed with solvent stream 211, which is contacted with stream 201 in a counter-current manner. An ethylene glycol and solvent rich stream 204 is removed. Subsequently, a diethylene glycol and solvent rich stream 208 and a triethylene glycol and solvent rich stream 212, optionally also containing higher ethylene glycols, are removed. A residual stream 215 is also removed for further purification, recycle or disposal.

Optionally, an extra aqueous stream 216 may be added to the extraction unit 214. The residual stream 215 may then be recycled and added to extra aqueous stream 216 before it is fed into extraction unit 214. In this case, the feed stream 201 may be located at any height (tray) in extraction unit 214, even below the ethylene glycol 204 or diethylene glycol 208 rich streams.

Figure 3:
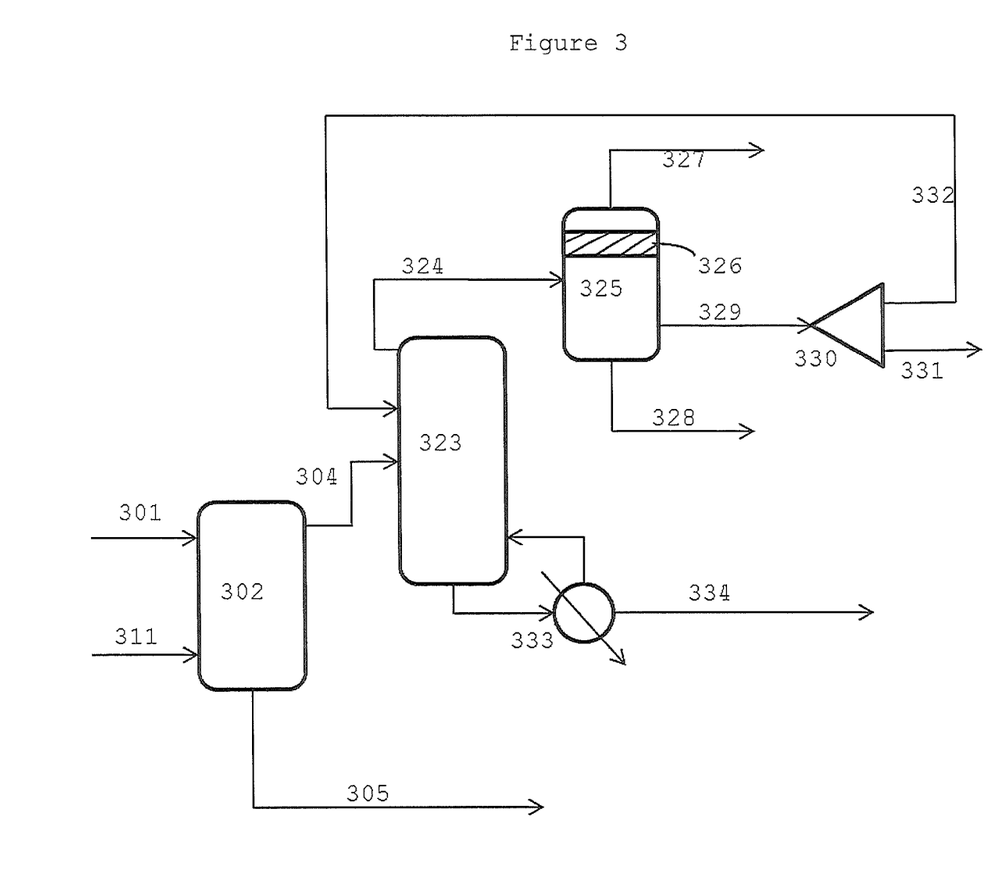

In a further embodiment illustrated in FIG. 3, the aqueous stream comprising the alkylene glycol and the corresponding dialkylene glycol comprises the reaction product stream from a process for the preparation of ethylene glycol from ethylene oxide. The stream contains at least MEG, DEG, TEG and higher ethylene glycols. This stream 301 is fed into a counter-current extraction unit 302. Said extraction unit is also fed with solvent stream 311, which is contacted with stream 301 in a counter-current manner.

Residual stream 305 is removed from the extraction unit and an ethylene glycol and solvent rich stream 304 is fed to a distillation unit equipped with a reboiler 333. MEG is removed as the bottom stream 334 from the distillation unit. This stream is essentially free of amine or, alternatively, is subjected to a further purification step.

A top stream 324 from the distillation unit 323 comprises amines and passes, optionally after condensing and/or cooling, to a decanter 325 where any water 328 is removed. The amine can then be split to provide a recycle stream 331 and an amine stream for reflux 332.

Any off-gas will be removed from the system via offgas stream 327.

Further optimisation of each of the embodiments exemplified in FIGS. 1 to 3 may be achieved by incorporating temperature control, specifically heaters and coolers, within or between each stage.

The present invention is further illustrated in the following Examples.

EXAMPLES

In each of the following examples, where relevant, to calculate the selectivity, the ratio of the concentration in the upper phase over the concentration in the lower phase was calculated (K-values). The solvent DMCA is the key component of the upper phase. The selectivity of the solvent for one component compared to a second component is the ratio of the K-value of the first component over the K-value of the second component.

Example 1

A solution of 10 wt % MEG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for MEG over water was 1.53 at 50° C.

Example 2

A solution of 20 wt % MEG and 2 wt % DEG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for DEG over MEG was 0.92 at 50° C.

Example 3

A solution of 20 wt % MEG and 2 wt % TEG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for TEG over MEG was 0.75 at 50° C.

Example 4

A solution of 20 wt % MEG and 2 wt % TTEG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for TTEG over MEG was 0.43 at 50° C.

Example 5

A solution of 5 wt % MEG in water was mixed with MP in a weight ratio of 1:1. This mixture was stirred at 50° C. for 30 minutes and after stopping the stirring two liquid phases quickly separated. Samples were taken from both liquid phases and analyzed by gas chromatography.

The selectivity of MP for MEG over water was 1.6 at 50° C.

Example 6

A solution of 5 wt % MEG in water was mixed with TEA in a weight ratio of 1:1. This mixture was stirred at 50° C. for 30 minutes and after stopping the stirring two liquid phases quickly separated. Samples were taken from both liquid phases and analyzed by gas chromatography.

The selectivity of MP for MEG over water was 1.1 at 50° C.

Figure 4:
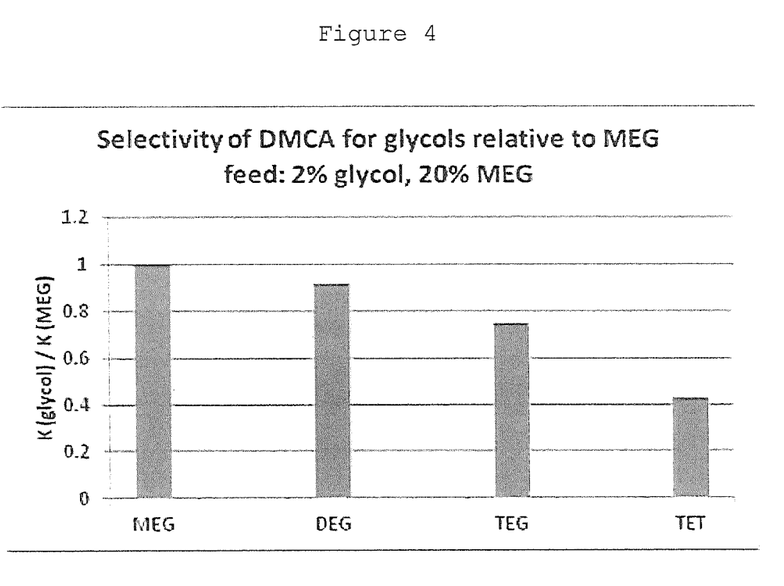
FIG. 4 is a graph demonstrating the selectivity of a specific amine to MEG and higher ethylene glycols.

The results of examples 1-4 are illustrated in FIG. 4. In FIG. 4, the selectivity for MEG is taken as 1 and the selectivity to the other glycols are in relation to that. It can be seen that the DMCA is most selective for MEG, while DEG, TEG and TTEG are extracted to a lesser extent.

That which is claimed is:
1. A process for the recovery of an alkylene glycol from an aqueous stream comprising an alkylene glycol and a corresponding dialkylene glycol, said process comprising the steps of providing the aqueous stream comprising the alkylene glycol and the corresponding dialkylene glycol, providing a first solvent stream, combining said aqueous stream comprising the alkylene glycol and the corresponding dialkylene glycol with said first solvent stream and recovering at least a portion of the alkylene glycol by liquid-liquid extraction, wherein said solvent stream comprises an amine selected from the group consisting of dimethyl-cyclohexyl amine, methyl cyclohexyl amine, 1-methyl piperidine, triethylamine, tripropylamine, or a combination thereof.

2. A process according to claim 1, wherein at least a portion of the alkylene glycol is recovered by liquid-liquid extraction by a process comprising the steps of extracting a portion of the alkylene glycol into the solvent and separating an alkylene glycol and solvent rich stream, leaving a first residual stream.

3. A process according to claim 2, wherein dialkylene glycol is subsequently recovered from the first residual stream by a process comprising the steps of providing the first residual stream, providing a solvent stream, combining said first residual stream with said solvent stream and recovering at least a portion of the dialkylene glycol by liquid-liquid extraction, wherein said solvent stream comprises the amine.

4. A process according to claim 3, wherein at least a portion of the dialkylene glycol is recovered by liquid-liquid extraction by a process comprising the steps of extracting a portion of the dialkylene glycol into the solvent and separating a dialkylene glycol and solvent rich stream, leaving a second residual stream.

5. A process according to claim 4, wherein at least one higher alkylene glycol is subsequently recovered from the second residual stream by a process comprising the steps of providing the second residual stream, providing a solvent stream, combining said second residual stream with said solvent stream and recovering at least a portion of the at least one higher alkylene glycol by liquid-liquid extraction, wherein the solvent stream comprises the amine.

6. A process according to claim 5, wherein at least a portion of the at least one higher alkylene glycol is recovered by liquid-liquid extraction by a process comprising the steps of extracting a portion of the at least one higher alkylene glycol into the solvent and separating a higher alkylene glycol or glycols and solvent rich stream, leaving a third residual stream.

7. A process according to claim 2, wherein the alkylene glycol and solvent rich stream is then separated into an alkylene glycol rich stream and a solvent rich stream by distillation.

8. A process according to claim 7, wherein the solvent in the solvent rich stream is separated from any water present therein by a process comprising phase separation.

9. A process according to claim 1, wherein dialkylene glycol is recovered from the aqueous stream comprising the alkylene glycol and the corresponding dialkylene glycol alongside the alkylene glycol.

10. A process according to claim 9, wherein at least a portion of the alkylene glycol and dialkylene glycol are recovered by liquid-liquid extraction by a process comprising the steps of extracting a portion of the alkylene glycol and dialkylene glycol into the first solvent stream and separating a glycol and solvent rich stream, leaving a first residual stream, and the glycol and solvent rich stream is subsequently subjected to at least one distillation step to separate the amine and the alkylene glycol and the dialkylene from each other.

11. A process according to claim 1, wherein the alkylene glycol is monoethylene glycol.

12. A process according to claim 3, wherein the dialkylene glycol is diethylene glycol.

13. A process according to claim 5, wherein the at least one higher alkylene glycol comprises triethylene glycol.

14. A process according to claim 1, wherein the solvent is selected from the group consisting of triethylamine, tripropylamine, or a combination thereof.

15. A process for the recovery of monoethylene glycol from an aqueous stream comprising monoethylene glycol and diethylene glycol, said process comprising:
combining the aqueous stream comprising monoethylene glycol and diethylene glycol with a first solvent stream comprising an amine selected from the group consisting of dimethyl-cyclohexyl amine, methyl cyclohexyl amine, 1-methyl piperidine, triethylamine, tripropylamine, or a combination thereof; and recovering at least a portion of the monoethylene glycol by liquid-liquid extraction.

16. A process according to claim 15, wherein recovering at least a portion of the monoethylene glycol by liquid-liquid extraction comprises: extracting a portion of the monoethylene glycol into the first solvent stream; and separating a monoethylene glycol and solvent rich stream, leaving a first residual stream comprising diethylene glycol.

17. A process according to claim 16, wherein diethylene glycol is subsequently recovered from the first residual stream by a process comprising: combining the first residual stream with a solvent stream comprising the amine; and recovering at least a portion of the diethylene glycol by liquid-liquid extraction.

18. A process according to claim 17, wherein recovering at least a portion of the diethylene glycol by liquid-liquid extraction comprises: extracting a portion of the diethylene glycol into the solvent stream; and separating a diethylene glycol and solvent rich stream, leaving a second residual stream comprising at least one higher ethylene glycol.

19. A process according to claim 18, wherein at least one higher ethylene glycol is subsequently recovered from the second residual stream by a process comprising: combining the second residual stream comprising the at least one higher ethylene glycol with a solvent stream comprising the amine; and recovering at least a portion of the at least one higher ethylene glycol by liquid-liquid extraction.

* * * * *